(12) United States Patent  (10) Patent No.: US 8,936,315 B2
Fienup et al.  (45) Date of Patent: Jan. 20, 2015

(54) OPHTHALMIC EXAMINATION CHAIR HAVING TILT DRIVE ASSEMBLY

(71) Applicant: Reliance Medical Products, Inc., Mason, OH (US)

(72) Inventors: William James Fienup, St. Louis, MO (US); Keith A. Grider, Chicago, IL (US)

(73) Assignee: Reliance Medical Products, Inc., Mason, OH (US)

( * ) Notice: Subject to any disclaimer, the term of this patent is extended or adjusted under 35 U.S.C. 154(b) by 36 days.

(21) Appl. No.: 13/655,856

(22) Filed: Oct. 19, 2012

(65) Prior Publication Data

US 2013/0099539 A1  Apr. 25, 2013

Related U.S. Application Data

(60) Provisional application No. 61/548,966, filed on Oct. 19, 2011.

(51) Int. Cl.

| | |
|---|---|
| *A61G 15/04* | (2006.01) |
| *A47C 1/035* | (2006.01) |
| *A61B 3/00* | (2006.01) |
| *A61G 15/02* | (2006.01) |
| *A61B 3/024* | (2006.01) |
| *A61G 5/10* | (2006.01) |
| *A61G 15/12* | (2006.01) |

(52) U.S. Cl.
CPC .............. *A61B 3/0083* (2013.01); *A61G 15/02* (2013.01); *A61B 3/024* (2013.01); *A61G 5/1075* (2013.01); *A61G 15/12* (2013.01)

USPC .......................................................... 297/330

(58) Field of Classification Search
CPC ..... A61G 15/02; A47C 1/0347; A47C 3/0257
USPC .......................................................... 297/330
See application file for complete search history.

(56) References Cited

U.S. PATENT DOCUMENTS

| | | | | |
|---|---|---|---|---|
| 2,874,689 | A | * | 2/1959 | Gavelek .......................... 601/99 |
| 3,135,550 | A | * | 6/1964 | Bosack .......................... 297/329 |
| 3,486,789 | A | | 12/1969 | Taylor et al. |
| 3,578,379 | A | | 5/1971 | Taylor et al. |
| 3,873,152 | A | | 3/1975 | Garas |
| 3,934,929 | A | * | 1/1976 | Rabinowitz ............... 297/330 X |
| 3,984,146 | A | * | 10/1976 | Krestel et al. .................. 297/330 |
| 3,999,799 | A | * | 12/1976 | Daswick ................... 297/330 X |
| 4,101,168 | A | * | 7/1978 | Ferro ........................ 297/330 X |
| 4,552,403 | A | * | 11/1985 | Yindra .......................... 297/330 |
| 4,572,573 | A | * | 2/1986 | Yoshikawa et al. ........ 297/330 X |
| 4,929,023 | A | * | 5/1990 | Rasmussen .................... 297/330 |
| 5,190,349 | A | * | 3/1993 | Austin et al. ............. 297/330 X |
| 5,348,375 | A | * | 9/1994 | Steininger ................ 297/362.11 |
| 5,480,212 | A | | 1/1996 | Marconet |
| 5,624,159 | A | * | 4/1997 | Celoni et al. .................. 297/325 |

(Continued)

*Primary Examiner* — Rodney B White
(74) *Attorney, Agent, or Firm* — Wood, Herron & Evans, L.L.P.

(57) ABSTRACT

An ophthalmic examination chair includes a seat for supporting a patient thereon, a support base for supporting the seat, a tilt guide assembly for tiltably moving the seat with respect to the support base, and a tilt driving assembly. The tilt driving assembly includes a motor operatively connected with a drive element and a drive transmission element operatively connected with the drive element. The drive transmission element is further operatively connected with the seat for moving the seat when the motor is activated.

7 Claims, 6 Drawing Sheets

(56) References Cited

U.S. PATENT DOCUMENTS

| | | | |
|---|---|---|---|
| 5,765,910 A * | 6/1998 | Larkin et al. | 297/172 |
| 5,907,387 A | 5/1999 | Schwaegerle | |
| 5,992,934 A | 11/1999 | Gehrig et al. | |
| 6,056,363 A * | 5/2000 | Maddox | 297/330 X |
| 6,106,065 A | 8/2000 | Carroll | |
| 6,382,725 B1 * | 5/2002 | Carroll | 297/330 |
| 6,450,578 B1 * | 9/2002 | Taggett | 297/325 |
| 6,916,065 B2 * | 7/2005 | Park | 297/330 X |
| 7,347,492 B2 * | 3/2008 | DiRe | 297/330 X |
| 7,448,680 B2 * | 11/2008 | DiRe | 297/330 X |
| 7,708,344 B1 * | 5/2010 | Broering et al. | 297/330 |
| 2012/0062011 A1 * | 3/2012 | Jones et al. | 297/362.11 |

* cited by examiner

OPHTHALMIC EXAMINATION CHAIR HAVING TILT DRIVE ASSEMBLY

RELATED APPLICATION

This application claims priority to U.S. Provisional Patent Application No. 61/548,966 filed Oct. 19, 2011, the disclosure of which is incorporated by reference herein in its entirety.

FIELD OF THE INVENTION

The present invention generally relates to ophthalmic examination chairs, such as those used during an eye examination. More particularly, the invention relates to examination chairs that allow a patient to be put into a tiled and reclined position.

BACKGROUND

During an eye examination, a series of tests are performed on a patient, who is typically seated in an examination chair. These tests can include an external examination of the eyes and surrounding tissues, tests to determine the acuteness or clearness of vision, examination of the pupils, and other examinations, tests or procedures pertaining to the eyes. Instruments are used during the eye examination and these instruments are typically retrieved from or stored on an associated instrument delivery stand positioned nearby the seated patient. For example, instrument delivery stands are known that include an instrument arm for presenting and positioning a table supporting an examination instrument in front of a patient. For example, a slit lamp machine may be supported on a table connected with an instrument arm, and is used by an eye doctor or other examiner to view different parts of the eye, including the cornea, the iris, the optic nerve, the retina, and the like.

For some stages of an eye examination, it may be desirable for a patient to be generally reclined rather than sitting upright in the examination chair. Accordingly, various examination chairs have been developed that provide adjustable seating positions. In a known example, an examination chair includes a back portion that pivots with respect to a seat portion are known. Examination chairs that provide a reclining seat portion are also known.

However, simple pivoting of a chair's back portion with respect to a seat portion might be uncomfortable for a patient and might not properly support the patient's body in the reclined position. A tilted and reclined position may be desirable in some circumstances, wherein a patient's entire body is tilted with respect to the upright seated position. Such a tilted and reclined position preserves the relative arrangement of the patient's body as when seated in the upright seated position, but provides the advantages of being reclined.

There is a need, therefore, for an ophthalmic examination chair that addresses one or more of the needs in the field of ophthalmic examination chairs and provides for appropriate tilted positioning of a patient during an eye examination.

SUMMARY OF THE INVENTION

According to one embodiment of the invention, an ophthalmic examination chair includes a seat for supporting a patient thereon, a support base for supporting the seat, a tilt guide assembly for tiltably moving the seat with respect to the support base, and a tilt driving assembly. The tilt driving assembly includes a motor operatively connected with a drive element and a drive transmission element operatively connected with the drive element. The drive transmission element is further operatively connected with the seat for moving the seat when the motor is activated.

According to another embodiment of the invention, a method is provided for adjusting an examination chair seat of an examination chair with respect to a support base. The chair further includes a tilt driving assembly associated with the seat, the tilt driving assembly including a motor operatively connected with a drive element and a drive transmission element operatively connected with the drive element, the drive transmission element being further operatively connected with the seat. The method includes activating a motor of the tilt driving assembly, engaging the drive element with the drive transmission element, and engaging the drive transmission element with the seat to move the seat, and tiltably moving the seat with respect to the base.

Various additional features and advantages of the invention will become more apparent to those of ordinary skill in the art upon review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE ILLUSTRATIVE EMBODIMENTS

Figure 1:
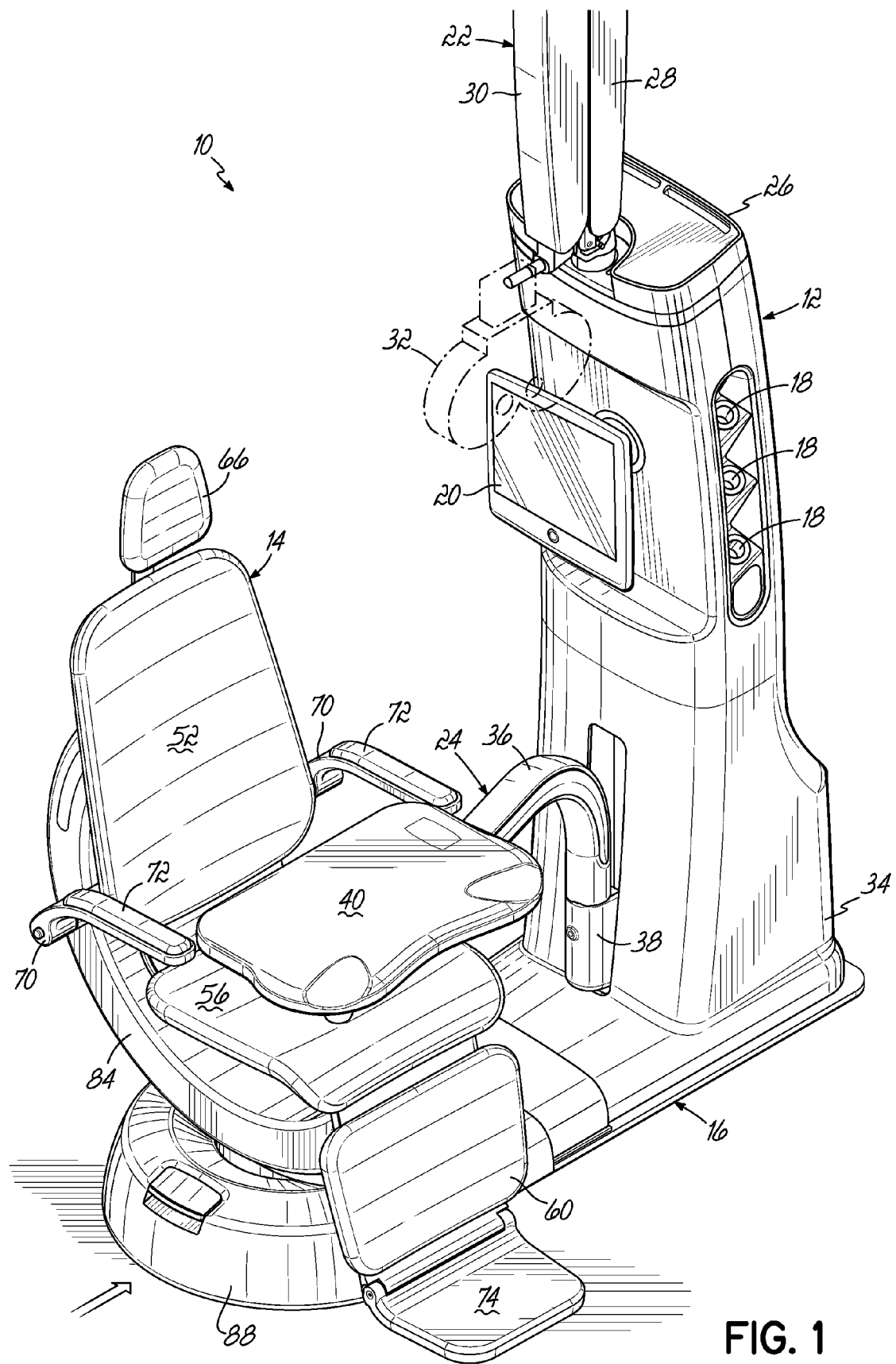
FIG. 1 is an isometric view of an exemplary eye examination suite in accordance with the principles of the present invention.
Figure 2:
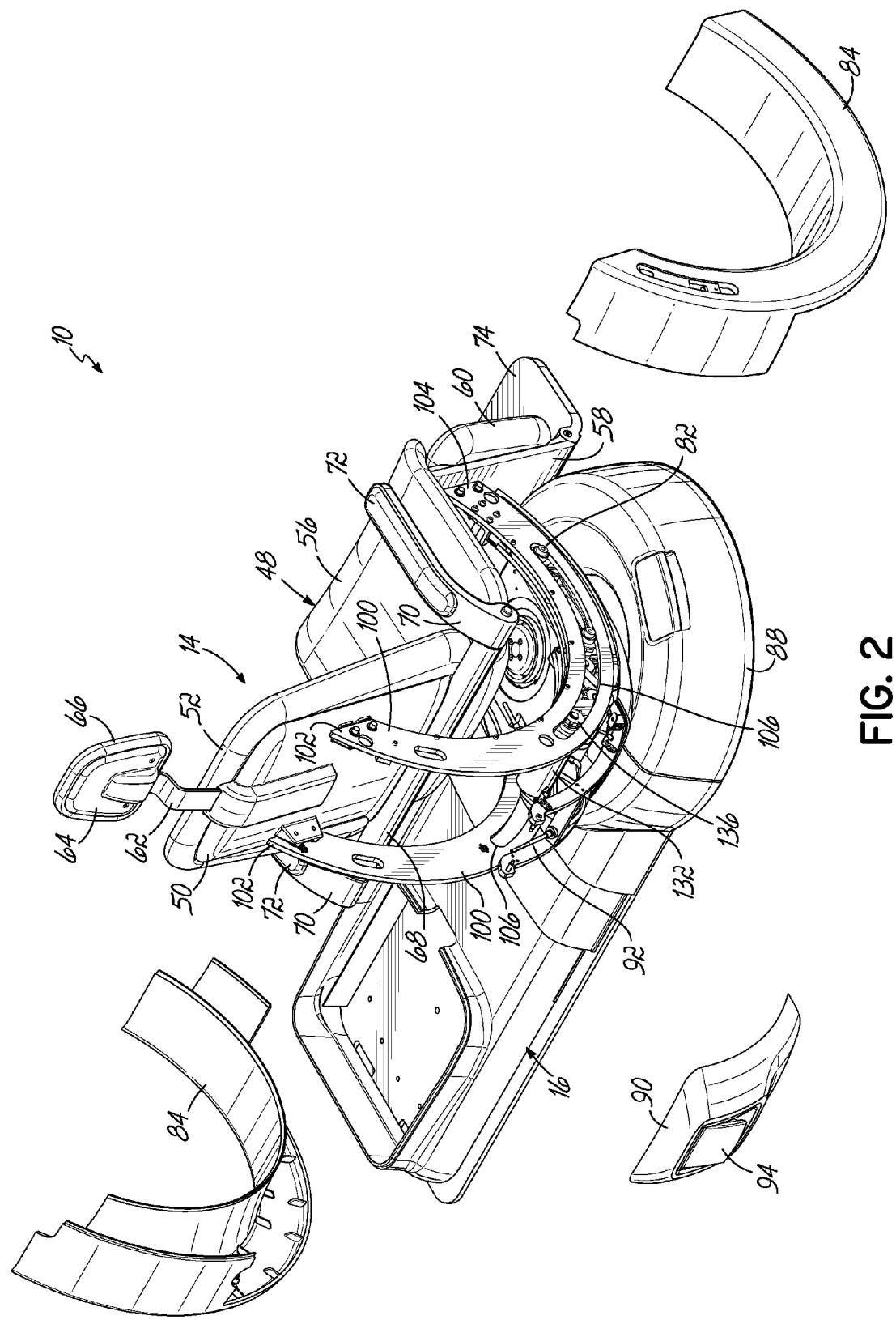
FIG. 2 is an exploded isometric view showing portions of an examination chair of the eye examination suite of FIG. 1 with cover portions removed.

Referring now to the figures, an exemplary eye examination suite in accordance with the principles of the present invention is shown and is indicated generally by the reference numeral 10. The eye examination suite 10 is of the type used for examinations and includes an instrument delivery stand 12, a chair 14 for a patient to sit in, and a base 16. The stand 12 and the chair 14 are connected through the base 16, as shown in the figures. During an eye examination, a patient may be seated in the chair 14 in a forward-facing direction, and an eye doctor or other practitioner may stand or be seated on a stool (not shown) generally in the region near the patient in the chair 14 and the stand 12.

As shown in FIG. 1, the stand 12 provides storage 18 for examination instruments, supports an information screen 20, and includes an upper instrument arm assembly 22 and a lower instrument arm assembly 24. The upper instrument arm assembly 22 extends from an upper region 26 of the stand 12 and includes a first arm portion 28, a second arm portion 30, and a phoropter 32. The first arm portion 28 is adjustably connected with the stand 12, and the second arm portion 30 is adjustably connected with the first arm portion 28. In addition, the phoropter 32 is adjustably connected with the second portion 30. Through these adjustable connections, the upper instrument arm assembly 22 is adjustable with respect to a seated patient and allows the physician or practitioner to position the phoropter 32 appropriately with respect to the patient's face and eyes during an eye examination. The upper instrument arm assembly 22 can also be placed into a stowed position adjacent the stand 12.

The lower instrument arm assembly 24 extends from a lower region 34 of the stand 12 and includes an arm 36 extending upwardly from a support 38, and an instrument supporting element, such as a table 40 (FIG. 1). The arm 36 is adjustably connected with the support 38, and the table 40 is adjustably connected with the arm 36. For example, the arm 36 is pivotably rotatable with respect to the support 38. Optionally, the arm 36 may be raised or lowered with respect to the base 16, such as by raising or lowering the support 38. Through these adjustable connections, the lower instrument arm assembly 24 is adjustable with respect to a seated patient and allows the physician or practitioner to position the table 40 (or any other instrument supporting element) appropriately with respect to the patient during an eye examination.

FIG. 1 shows the chair 12 in an upright position in which a patient would be seated in an upright, seated position. In some circumstances, it may be desirable to situate a patient in a tilted and reclined position relative to the upright, seated position.

Referring to FIGS. 2-5, the chair 14 includes a seat 48 that includes several spine portions, with each spine portion supporting a cushion thereon. In particular, an upper spine portion 50 supports a back cushion 52, a seat spine portion 54 supports a seat cushion 56, and a lower spine portion 58 supports a leg cushion 60. A neck 62 extends upwardly from the upper spine portion 50 and supports a headrest spine portion 64, which supports a headrest cushion 66. An elongate arm support portion 68 is attached proximate a lower end of the upper spine portion 50 and extends between opposite sides of the chair 14 to support arm rests 70. Arm rests 70 include arm rest cushions 72. The chair 14 also includes a foot rest 74 that may be upwardly pivoted with respect to the lower spine portion 58.

The upper spine portion 50, the seat spine portion 54, the lower spine portion 58, and the headrest spine portion 64 are connected in a manner that prevents moment of these portions relative to one another. Accordingly, the positions of the upper spine portion 50, the seat spine portion 54, the lower spine portion 58, and the headrest spine portion 64 relative to one another are maintained even though the seat 48 may be tilted to different inclinations as described more fully below. Because the relative orientation of these spine members of the seat 48 is maintained, the seat 48 generally maintains the relative arrangement of a patient's body who sits in the seat 48, even when the seat 48 is tilted.

The chair 14 also includes a chair support base 80 that supports the seat 48. The chair support base 80 includes guides a tilt guide assembly 81 that provides for tilting of the seat 48 with respect to the support base 80. In particular, the tilt guide assembly 81 includes a track and guide arrangement, with a track component interacting with a guide component to guide the tilting movement of the chair 48. In the embodiment shown, the tilt guide assembly 81 includes guides, such as rollers 82 on the support base 80, for supporting and guiding the tilting movement of the seat 48, as will be explained. The rollers 82 rotate along axes generally parallel to a floor underlying the chair 14. The chair support base 80 may also optionally include features for raising and lowering the seat 48 in the vertical direction, or for allowing the seat 48 to swivel around a vertical axis.

As best seen in FIGS. 2-4A, the chair 14 includes a number of cover portions. In particular, side cover portions 84 cover a seat frame assembly 86, chair support base cover portions 88 cover the chair support base 80, and a swivel handle cover portion 90 covers a swivel control assembly 92. Swivel control assembly 92 includes a handle 94 for selectively disengaging the chair 14 from a fixed swivel position and allowing the chair 14 to swivel about a vertical axis. The cover portions 84, 88, and 90 may generally be selected to provide the chair 14 with desired aesthetic characteristics, and it will be readily appreciated that additional cover portions for covering various other features of the chair 14 could also be used.

Figure 3:
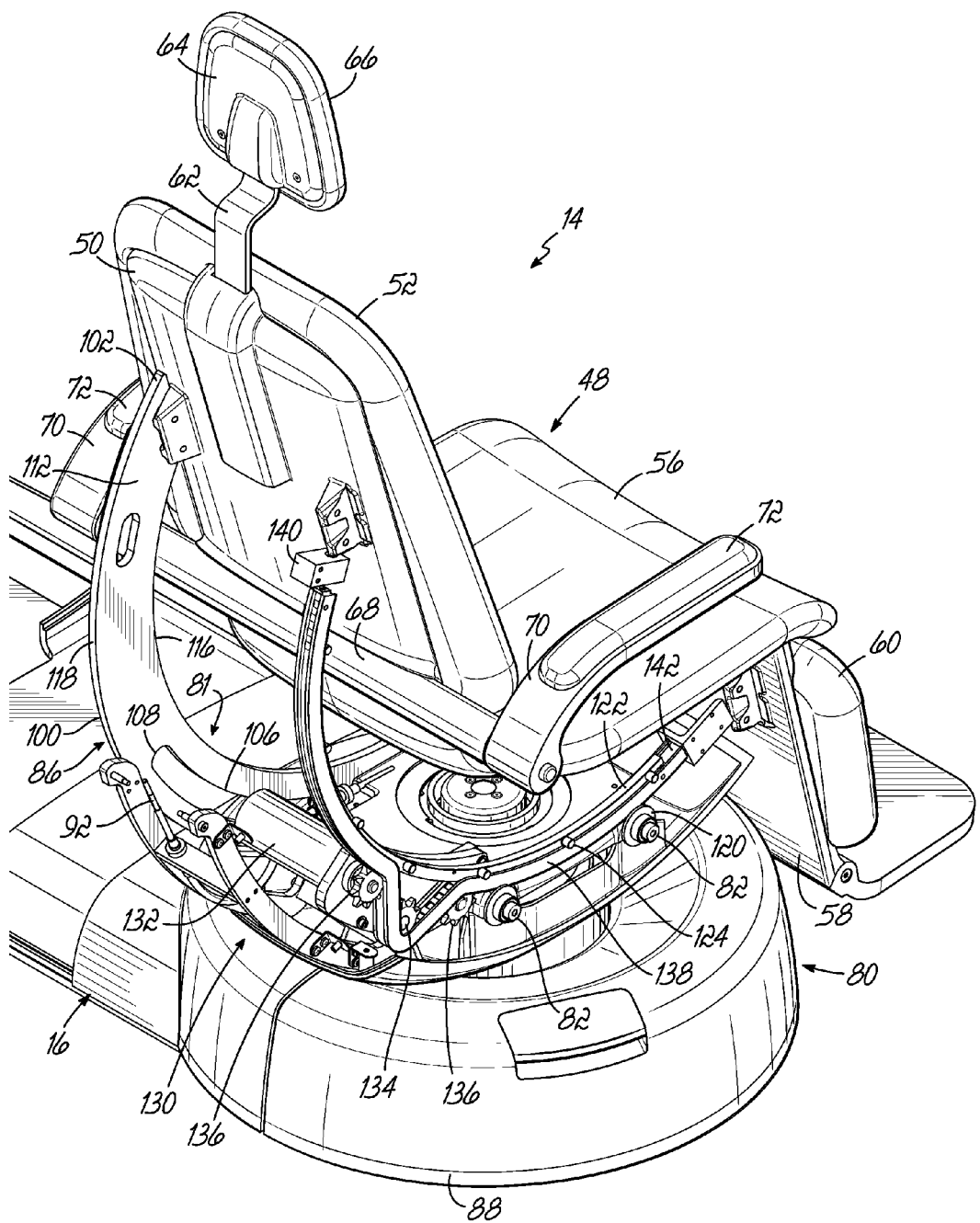
FIG. 3 is a partial disassembled view of the examination chair shown in FIG. 2, with a frame arm removed to show features of a tilt driving assembly.
Figure 4A:
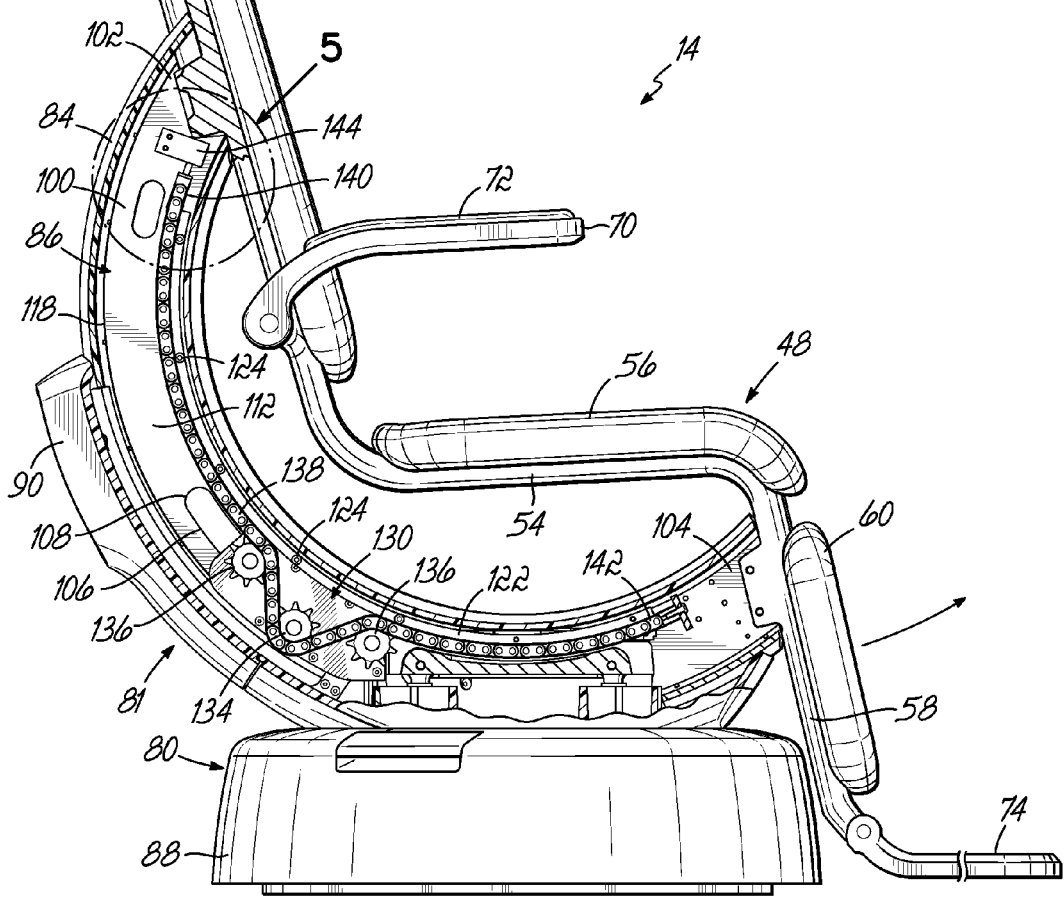
FIG. 4A is a partial cross-sectional view of the examination chair shown in FIG. 3.
Figure 4B:
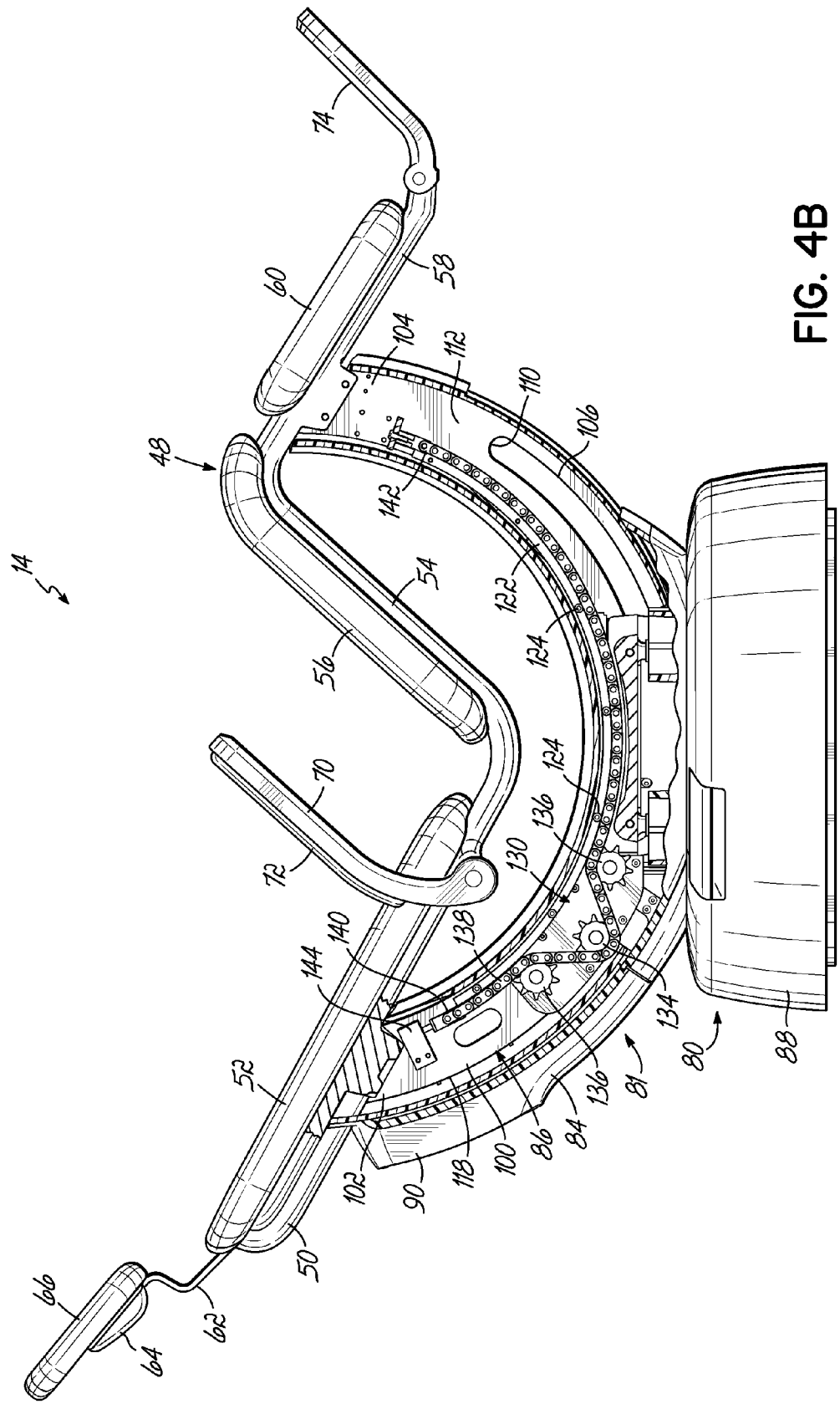
FIG. 4B is view similar to FIG. 4A, but with the examination chair in a tilted and reclined position.

The frame assembly 86 includes a pair of substantially similar frame arms 100. Each frame arm 100 has a generally planar and rigid construction and has a curved shape that extends from a first end 102 to a second end 104. The frame assembly 86 supports, and is attached to, the seat 48 near the first ends 102 and near the second ends 104 of the frame arms 100 (FIG. 4A). In particular, the frame assembly 86 is attached at first ends 102 to the upper spine portion 50, and at second ends 104 to the lower spine portion 58. Each frame arm 100 includes a curved slot 106 that extends in the frame arm 100 from a first end 108 to a second end 110. Each frame arm 100 also generally includes a frame arm inner surface 112 (FIG. 4A), a frame arm outer surface 114 (FIG. 5), a frame arm upper surface 116 (FIG. 3), and a frame arm lower surface 118 (FIG. 3). The slots 106 extend through the frame arms 100 from the inner and outer surfaces 112, 114, and between the upper and lower surfaces 116, 118.

The frame assembly 86 engages the chair support base 80 with the rollers 82 being received in the curved slots 106. Accordingly, the rollers 82 support the portion of the chair 14 that is attached to the frame assembly 86 (including the seat 48). In addition, when a patient is seated in the chair 14, the rollers 82 also support the patient. This arrangement with the rollers 82 received in the curved slots 106 provides for the frame assembly 86 to be moveable with respect to the chair support base 80, and in particular, to be tiltably moveable along a path defined by the curved slots 106, with the tilting movement being aided by the rollers 82.

The general direction of the tilting movement of the seat 48 is indicated by the arrows in FIG. 4A. The extent of the tilting movement may be defined by the selective positioning of the first and second ends 108, 110 of the curved slots 106. For example, the first end 108 may define an extent of tilted movement in one direction when the first ends 108 abut the rollers 82. Similarly, the second end 110 could define another extent of tilted movement in the opposite direction when the second ends 110 abut the rollers 82. In the embodiment shown, the rollers 82 include enlarged flange portions 120 (FIG. 3) that extending beyond the dimension of the curved slots 106, such as beyond the outer surfaces 114 of the frame arms 100.

While the frame arms 100 have been shown and described herein as having slots 106 cooperating with the rollers 82, it will be appreciated that various other structure for guiding the tilting movement of the seat 48 between upright and reclined positions may alternatively be used. As a non-limiting example, the frame arms 100 could have curved grooves instead of slots, and the rollers 82 could be received in the grooves. And in even other embodiments, the frame assembly 86 could carry guides (such as rollers) for engaging slots or grooves on the chair support base 80. The frame assembly 86 and the chair support base 80 together provide cooperating structure that provides the frame assembly 86 (and therefore the seat 48 supported thereon) to be tiltably moveable with respect to the chair support base 80. In view of the fact that these cooperating structures can have many forms, their combination can be generally referred to as a track and guide assembly, as introduced above. In some embodiments, the frame arms 100 of the frame assembly 86 can include track components and the chair support base 80 can include guide components, and in other embodiments, the frame arms 100 can include the guide components and the chair support base 80 can include the track components.

In the embodiment shown, each frame arm 100 further includes a guide rail 122 extending along a curved pathway on the frame arm inner surface 112 generally between the curved slot 106 and the frame arm upper surface 116 (FIG. 4). The guide rail 122 is attached to the frame arm 100 by fasteners 124, but could alternatively be formed integral with the frame arm 100. The guide rail 122 provides a curved guiding pathway for a drive transmission element used to tiltably move the seat 48.

With reference to FIGS. 3, 4A, 4B, and 5, the chair 14 also includes a tilt driving assembly 130 that includes a motor 132 having a drive element 134 such as a gear, one or more optional idler gears 136, and a drive transmission element 138. As depicted, the tilt driving assembly 130 is generally positioned between the frame arm inner surfaces 112 of the frame arms 100. The drive transmission element 138 is fixedly attached to a frame arm 100 near the drive transmission element's first end 140 and near its second end 142. As depicted in the figures, the first end 140 of the drive transmission element 138 is attached near the first end 102 of the frame arm 100, and the second end 142 of the drive transmission element 138 is attached near the second end 104 of the frame arm 100.

Figure 5:
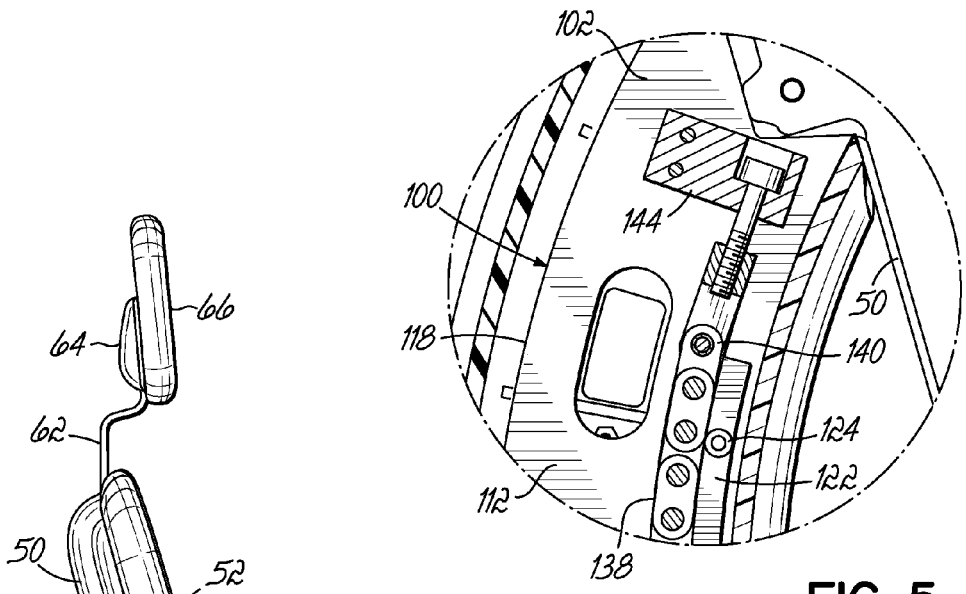
FIG. 5 is an enlarged view of the encircled area of FIG. 4A.

Drive transmission element 138 may be a chain, such as shown in the figures, or may be any suitable structure for transmitting the driving force of the motor 132 to the frame arm 100, such as a belt. Optionally, a suitable drive transmission element may be integrated more directly into the frame arm 100, such as by forming gear teeth on the frame arm 100 or into the guide rail 122. The structure of the drive element 134 is chosen to be compatible with the drive transmission element 138, and for the chain drive transmission element shown in the figures, the drive element 134 is in the form of a toothed sprocket gear having teeth that engage the links in the chain, or drive transmission element 138. Suitable alternative combinations for a drive element and drive transmission element might also be used. The idler gears 136 are used to redirect the direction of the drive force created by the motor 132, if desired. In some embodiments, idler gears may not be included and the drive element 134 of the motor 132 may directly engage and drive the drive transmission member 138. Optionally, a tensioner 144 may be included for adjusting the tension in the drive transmission element 138, such as shown in FIG. 5 near the first end 140 of the drive transmission element 138.

The drive transmission element 138 generally extends along the curved pathway of the guide rail 122 between the guide rail 122 and the curved slot 106. The motor 132 drives the drive transmission element 138 essentially along that pathway (with minor deviations from the pathway if the idler gears 136 are present). Thus, when the motor 132 is actuated to rotate the drive element 134 in a counter-clockwise direction (as viewing in FIGS. 4A and 4B) the drive element 134 engages the drive transmission element 138 and the frame arm 100 is moved along with its attached drive transmission element 138 so the seat 48 is tilted in the direction of a reclined position. Similarly, when the motor 132 is actuated to rotate the drive element 134 in a clockwise direction, the drive element 134 engages the drive transmission element 138 and the frame arm 100 is moved so the seat 48 is tilted in the direction of the upright position.

While the chair 14 shown and described herein includes a guide rail 122, it will be appreciated that the guide rail 122 may not be required, such as when the drive transmission element 138 is fixedly attached to a frame arm 100 along an appropriately-shaped pathway.

The motor 132 may be selected based on a number of factors, with consideration given to the amount of weight that the motor may be called upon to move, such as the weight of the chair's seat and a patient. Generally, a motor could be chosen that provides more than sufficient power or torque to operate the chair 14 with any conceivable patient seated thereon. In some embodiments, a motor may be chosen that is capable of using back EMF to lock the rotation of the motor's drive shaft, which would tend to prevent the seat 48 from tilting when the motor is not moving, as the drive transmission element 138 would not be able to move. Alternatively, the motor 132 may be associated with a gearing system for changing the rotational output characteristics of the motor. Such arrangements are sometimes referred to as gearmotors. In some embodiments, the motor 132 may be a 12 V DC gearmotor, such as one sold by Groschopp, Inc. of Sioux Center, Iowa. An example of a suitable Groschopp gearmotor has part number PM6015-PS1990. Exemplary characteristics of a suitable Groschopp gearmotor include providing 128 inch-pounds of torque at 8.8 revolutions per minute. Such a gearmotor provides more torque than is necessary for operation of the chair 14, even when the chair 14 includes a patient. The motor also may also include features for preventing its output shaft from rotating when the gearmotor is off, which may be achieved by shorting the windings and using back EMF to prevent rotation. Other suitable motors or gearmotors are generally available in the marketplace.

The operation of the tilt driving assembly 130 and the activation of the motor 132 may be actuated by any suitable controls, such as switches, a touch screen display, foot pedals, or various other controls, the implementation of which will be apparent to one of ordinary skill.

Figure 6A:
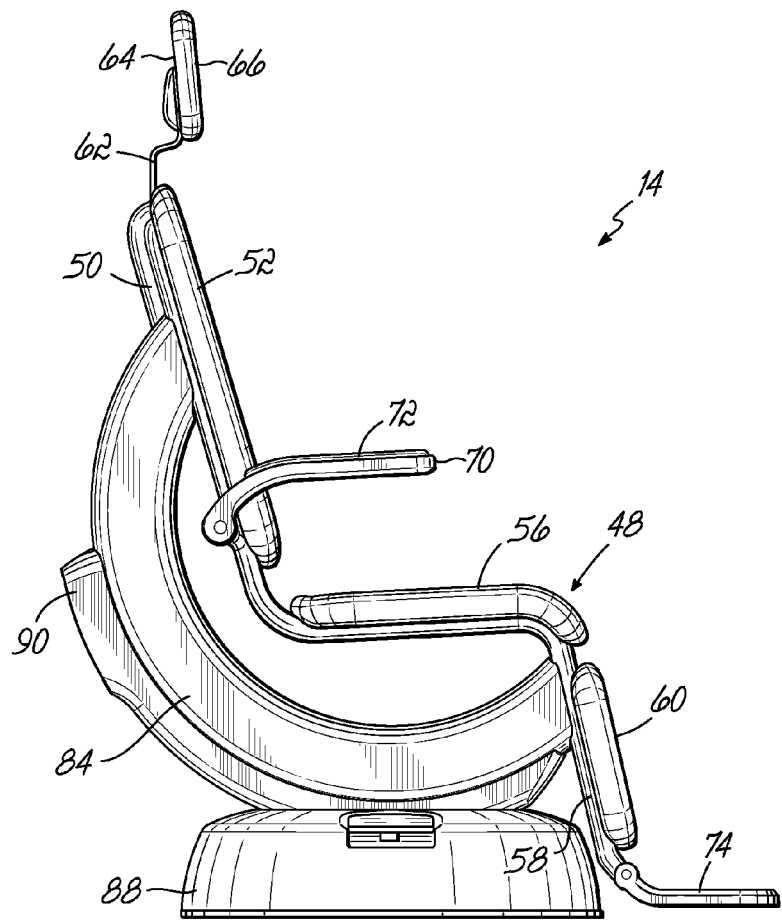
FIG. 6A is a side elevation view of the examination chair of FIG. 3 in a generally upright position.
Figure 6B:
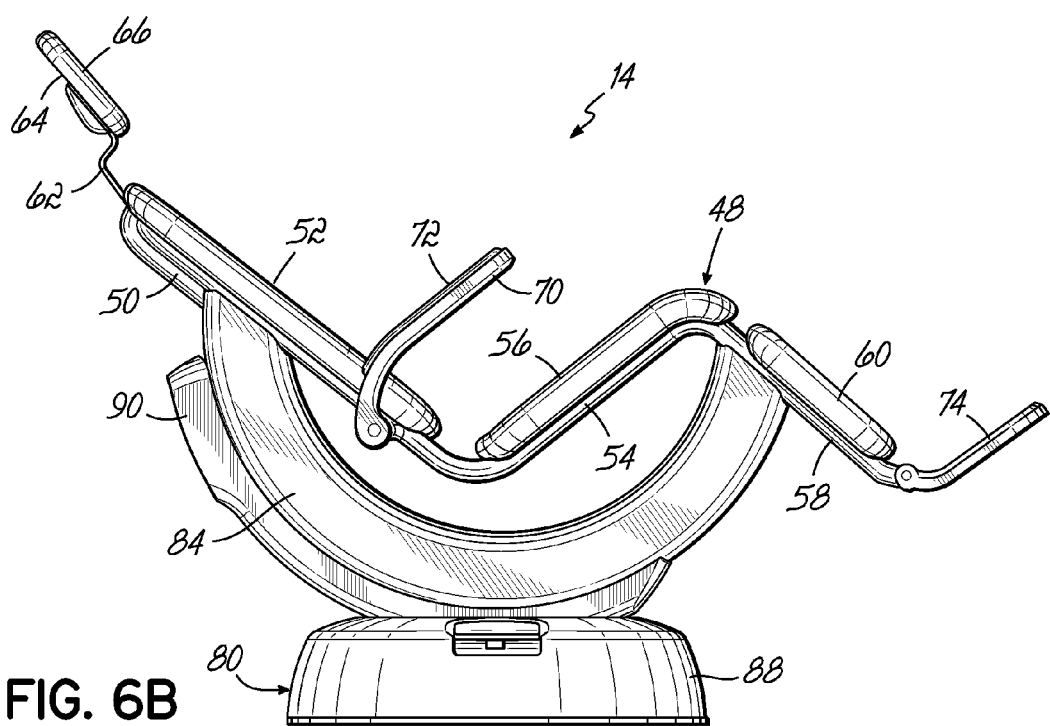
FIG. 6B is a side elevation view of the examination chair of FIG. 3 in a tilted and reclined position.

With reference to FIG. 6A, the chair 14 is shown with the seat 48 in a generally upright position. And in FIG. 6B, the chair 14 is shown with the seat 48 in a tilted and reclined position, such as what can be achieved by using the tilt driving assembly 130 to move the frame assembly 86 along a path defined by the curved slots 106 in the frame arms 100.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. An ophthalmic examination chair comprising:
   a seat for supporting a patient thereon,
   a support base for supporting the seat,
   a tilt guide assembly for tiltably moving the seat with respect to the support base,
   a tilt driving assembly including a motor operatively connected with a drive element and an elongate, curved drive transmission element directly connected with the drive element, wherein the elongate, curved drive transmission element is further operatively connected with the seat for moving the seat when the motor is activated, and
   a frame assembly, the seat supported by the frame assembly, the frame assembly including an elongate, curved frame arm, the elongate, curved drive transmission element extending lengthwise along the elongate, curved frame arm to define a curved path, and the elongate, curved drive transmission element being driven by the drive element when the motor is activated to tiltably move the seat along the curved path.

2. The ophthalmic examination chair of claim 1, wherein the elongate, curved frame arm is a first elongate, curved frame arm and the frame assembly further including a second elongate, curved frame arm, the tilt guide assembly including track components associated with the first and second elongate, curved frame arms and guide components associated with the support base.

3. The ophthalmic examination chair of claim 2, the track components including a curved slot formed in each of the first and second elongate, curved frame arms and the guide components including rollers carried by the support base, the rollers engaging the curved slots.

4. The ophthalmic examination chair of claim 1,
   wherein the drive transmission element is integrated with the elongate, curved frame arm.

5. The ophthalmic examination chair of claim 1,
   wherein the motor provides more torque than is necessary for moving the seat.

6. The ophthalmic examination chair of claim 1,
   wherein the motor provides 128 inch-pounds of torque at 8.8 revolutions per minute.

7. The ophthalmic examination chair of claim 1, wherein the motor is capable of using back EMF to lock the rotation of the motor's drive shaft for preventing movement of the seat.

\* \* \* \* \*